United States Patent [19]

DeBarbieri et al.

[11] Patent Number: 4,508,710

[45] Date of Patent: Apr. 2, 1985

[54] IN VITRO AND IN VIVO TREATMENT OF CANCER CELLS AND TREATMENT OF VIRUSES WITH A TRIPEPTIDE COMPOUND

[75] Inventors: Augusto DeBarbieri, Milan, Italy; Julius G. Bekesi, Teaneck, N.J.

[73] Assignee: Proter S.p.A., Milan, Italy

[21] Appl. No.: 468,036

[22] Filed: Feb. 23, 1983

Related U.S. Application Data

[63] Continuation-in-part of Ser. No. 455,477, Jan. 4, 1983, abandoned, which is a continuation-in-part of Ser. No. 311,646, Oct. 15, 1981, Pat. No. 4,428,875, which is a continuation-in-part of Ser. No. 173,621, Jul. 30, 1980, Pat. No. 4,314,999, which is a continuation-in-part of Ser. No. 929,237, Jul. 31, 1978, Pat. No. 4,216,208.

[51] Int. Cl.³ .................... A61K 37/02; C07C 103/52
[52] U.S. Cl. ............................ 514/19; 260/112.5 R
[58] Field of Search .................. 424/177; 260/112.5 R

[56] References Cited

U.S. PATENT DOCUMENTS 4,216,208  8/1980  DeBarbieri ................... 424/177
4,314,999  2/1982  DeBarbieri ................... 424/177

Primary Examiner—Blondel Hazel
Attorney, Agent, or Firm—Fisher, Christen & Sabol

[57] ABSTRACT

The cancericidal activity of all the permutations of a tripeptide compound formed from dichlorodiethylaminophenylalanine, parafluorophenylalanine and methionine bonded together with peptide links was demonstrated using seven in vitro tumor cell lines. The viabilities of each of the tumor cell lines were significantly reduced by treatment for 1 to 24 hours with 1 to 50 μg of the tripeptide per ml of carrier solvent. A pulse exposure to the tripeptide demonstrated that the reductions in tumor cell was comparable to continuous exposure. Other in vitro tests were all conducted on AKR mice.

Methods of treating virus by exposing the virus to one of the noted tripeptide compounds is also contemplated.

Methods of treating tumor cells with the tripeptides dissolved in a solvent consisting of dimethylacetamide, propylene glycol and absolute ethanol are also contemplated by the present invention.

17 Claims, 11 Drawing Figures

IN VITRO AND IN VIVO TREATMENT OF CANCER CELLS AND TREATMENT OF VIRUSES WITH A TRIPEPTIDE COMPOUND

RELATED APPLICATIONS

This application is a continuation-in-part of copending application U.S. Ser. No. 455,477 filed Jan. 4, 1983; now abandoned, which is a continuation in part of copending application U.S. Ser. No. 311,646, filed Oct. 15, 1981 now U.S. Pat. No. 4,428,875; which is a continuation-in-part of U.S. application Ser. No. 173,621, filed July 30, 1980, now U.S. Pat. No. 4,314,999; which is a continuation-in-part of application Ser. No. 929,237, filed July 31, 1978, now U.S. Pat. No. 4,216,208.

BACKGROUND OF THE INVENTION

1. Field of the Invention

The present invention relates to methods of treating different types of cancer cells either in vitro or in vivo by treatment with a tripeptide in which the amino acid dichlorodiethylaminophenylalanine is bonded by peptide links to parafluorophenylalanine and methionine.

2. Prior Art

Chemotherapy has been and still is an object of intense research. Certain positive results have undoubtedly been achieved, especially by means of polychemotherapy realized by associating different active substances according to carefully developed protocols. However, the ideal therapy has not been found. The need to find new active substances has been particularly emphasized. All the foregoing justifies continuous research directed toward preparing new chemotherapeutic compounds active against cancerous tumors. There are already known peptides having anti-tumor activity, consisting of both normal and antimetabolic amino acids, coupled by means of a peptide bond. Such peptides have for years been in therapeutic use with favorable results both in monochemotherapy and in polychemotherapy.

As disclosed in copending U.S. application Ser. No. 311,646, a new family of antitumor compounds is characterized in that each compound comprises the amino acids dichlorodiethylaminophenylalanine, parafluorophenylalanine and methionine bonded together by CO—NH peptide links formed by the respective amino and carboxyl groups of the said amino acids.

All possible permutations of the three amino acids are set forth as follows:

1. pFPne.MPhe.Met
2. pFPhe.Met.MPhe
3. MPhe.pFPhe.Met
4. MPhe.Met.p.FPhe
5. Met.pFPhe.MPhe
6. Met.MPhe.p.FPhe wherein "MPhe" indicates the amino acid dichlorodiethylaminophenylalanine having the structural formula:

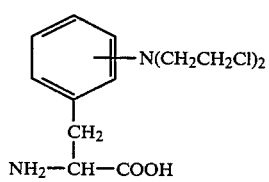

and wherein "pFPhe" indicates the amino acid parafluorophenylalanine having the structural formula:

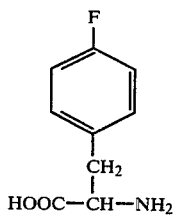

and wherein "Met" indicates the amino acid methionine having the structural formula:

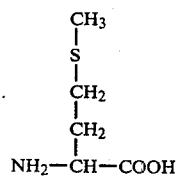

The above-identified tripeptides are useful in the treatment of malignant tumors. The above noted tripeptides are prepared by condensing one of the amino acids having a blocked amine group with another of said amino acids having a blocked carboxyl group with the aid of dicyclohexylcarbodiimide; removing one of the blocking groups to form a dipeptide having a blocked amine or carboxyl group; and condensing the dipeptide with the third amino acid to form the tripeptide with the aid of dicyclohexylcarbodiimide. Compounds of the tripeptide can also be formed, such as compound, by esterifying the tripeptide; and introducing hydrogenchloride.

To further illustrate the synthesis of a tripeptide compound, the following specific process is set forth.

CHEMICAL SYNTHESIS

Synthesis of N-formyl-3-(p-fluorophenyl)-L-alanyl-3-[m-bis(2-chloroethyl)aminophenyl]-L-alanine ethyl ester.
Depeptide I by Reaction I

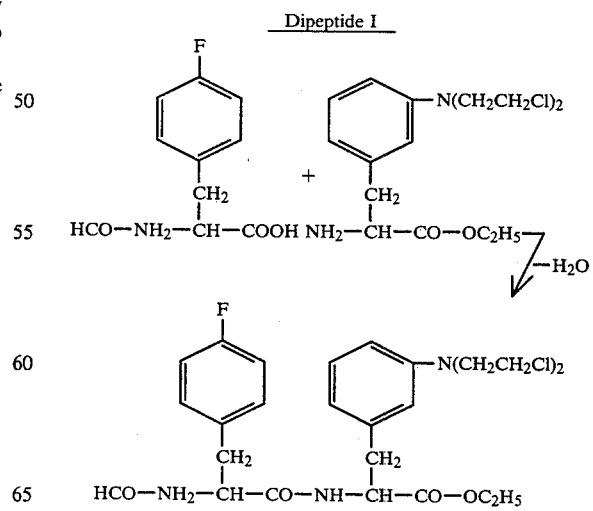

To m-bis(2-chloroethyl)aminophenyl-L-alanine ethyl ester [25.88 g] in 150 ml of tetrahydrofuran [15.37 g°], 3-(p-fluorophenyl)-L-alanine [17.18 g] and of N,N-dicyclohexylcarbodiimide (coupling agent) [15.85 g] were added successively while stirring for 15 minutes at 0° C. Temperature was then allowed to rise to 20° C. and the reaction mixture was held at this condition for 5 hours. At the completion of the reaction dicyclohexylurea was removed by filtration and the filtrate was evaporated at 40° C. at a reduced pressure. Residue then was recovered by adding ethyl ether (150 ml) and the precipitate was recovered by filtration, and vacuum dried at 40° C. The raw substance was further purified by crystallization in 96% ethyl alcohol yielding a white crystalline substance (Dipeptide I) with MP 126°–7° C. Analysis showed a molecular composition of $C_{25}H_{30}FCl_2N_3O_4$ (M=526.44). The calculated molecular composition of the substance in %: C: 57.04-H: 5.74-N: 7.98-Cl: 13.47; and found %: C: 56.88-H: 5.71-N: 8.01-Cl: 13.32. The overall yield of the reaction was 73% Dipeptide I.

Synthesis of
N-formyl-3-(p-fluorophenyl)-L-alanyl]-3-[m-bis(2-chloroethyl)aminophenyl]-L-alanine. Dipeptide II by Reaction II Dipeptide II Dipeptide I + NaOH $\xrightarrow[-C_2H_5OH]{HCL}$

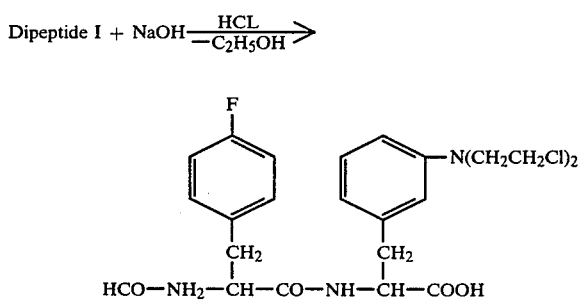

The white crystalline substance [26.3 g] (Dipeptide I) from Reaction I was dissolved in acetone [130 ml] by gently heating at 40° C. After cooling it to room temperature, 50 ml of 1N NaOH was added while stirring for 1 hour at 20° C. The hydrolysis reaction was monitored with TLC using a mixture of ethyl alcohol/ethyl acetate/acetic acid: 50:50:1 (v/v/v) solvent system. At the completion of reaction, 50 ml of 1N HCl were slowly added. The white precipitate (Dipeptide II) thus formed was separated by filtration and washed with water until disappearance of Cl from the filtrate. The thus obtained substance was first air dried then vacuum dried. The white amorphous substance had the following characteristics: MP 203°–206° C., a molecular composition of $C_{23}H_{26}FCl_2N_3O_4$ (M=498.39). The calculated composition in %: C: 55.43-H: 5.26-N: 8.43-Cl: 14.23, found %: C: 55.17-H: 5.24-N: 8.47-Cl: 14.81. The yield of Reaction II was 95% of Dipeptide II.

Synthesis of
3-(p-fluorophenyl)-L-alanyl-3-[m-bis(2-chloroethyl)aminophenyl]-L-alanyl-L-methionine ethyl ester.
Tripeptide III by Reaction III

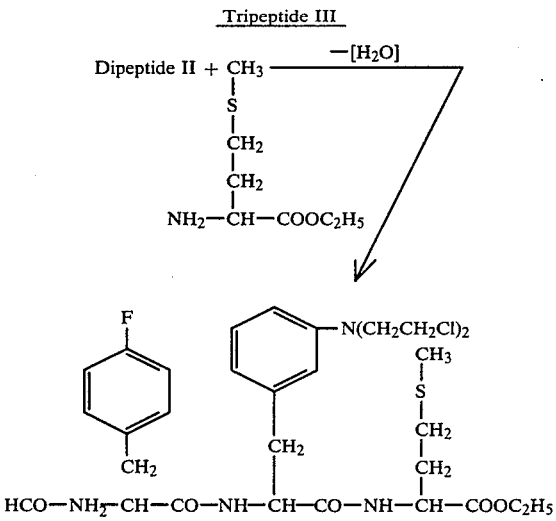

Dipeptide II (27.7 g) derived from reaction II was dissolved in 225 ml of N,N-dimethylformamide at 40° C. After cooling it to 15° C., a solution of L-methionine ethyl ester [10.28 g] in 20 ml of N,N-dimethylformamide was added, followed by successive addition of N-hydroxysuccinimide [8.6 g] and N,N-dicyclohexylcarbodiimide [12.57 g] in 25 ml of N,N-dimethylformamide. The thus obtained mixture was held at 5° C. for 30 minutes while stirring. Then the temperature was allowed to rise to 20° C. Dicyclohexylurea was removed by filtration, and to the filtrate while stirring, 1800 ml of water was added at 15° C. After washing, the filtrate was air dried and then successively kept under vacuum in the presence of $P_2O$ at 40° C. Purification of the crude substance was achieved by suspending it in 120 ml of absolute ethyl alcohol and solubilized by adding small portions of N,N-dimethylformamide and suspended for 15 hours at 5° C. The crystalline product was filtered and washed with absolute ethyl alcohol and dried under vacuum at 40° C. The white crystalline substance, Tripeptide III had the following properties: MP 187°–189° C., an analysis showing $C_{30}H_{39}FCl_2N_4O_5S$ (M=657.64), with-calculated composition (%) C: 54.79-H: 5.98-N: 8.51-Cl: 10.78-S: 4.87. Found (%): C: 54.03-H: 5.89-N: 8.52-Cl: 10.71-S: 4.84.

Synthesis of
3-(p-fluorophenyl)-L-alanyl-3-[m-bis(2-chloroethyl)aminophenyl]-L-alanyl-L-methionine ethyl ester HCl.
Tripeptide IV compound by Reaction IV

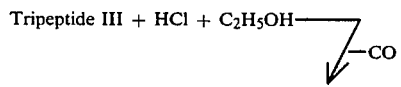

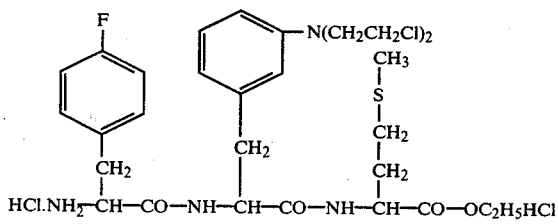

Tripeptide III [17.75 g] from Reaction III was suspended in 250 ml HCl solution (4.1% w/v) in absolute ethyl alcohol and was stirred for 4 hours at 20° C. The reaction mixture was held for 15 hours at 5° C. The course of hydrolysis reaction was monitored with TLC using ethyl ester/acetic acid/water=135:27:9 (v/v/v) solvent system. At the completion of the reaction, to the resulting clear solution 250 ml of water were slowly added while stirring and maintaining the pH at 3-3.2 with $NaHCO_3$ at 5° C. After 20 minutes agitation, the white bulky substance was filtered followed by washing with cold water at 5° C. The sample was first air dried, then vacuum dried at 40° C. in the presence of $P_2O_5$. Purification of the crude product was performed. Crystallization in isopropyl alcohol at 60°–65° C. was conducted after which the product in the isopropyl alcohol was cooled for 16 hours, at 15° C., filtered, washed first with isopropyl alcohol, then with acetone and dried under vacuum at 40° C. for 8 hours. The analysis of the resulting white crystalline substance (the tripeptide compound) showed the following characteristics MP 180°–182° C.; Analysis: for $C_{29}H_{39}Cl_2FN_4O_4SHCl$ (MW=666.08); Calculated %: C: 52.29-H: 6.05-N: 8.41-Cl: 15.97-S: 4.81; Found %: C: 52.31-H: 6.09-H: 8.38-Cl: 15.85-S: 4.76.

SUMMARY OF THE INVENTION

All six of the specific tripeptide compounds have similar characteristics and results in treating malignant tumor cells as well as viruses. For the purposes of simplification, only the tripeptide compound set forth previously in the chemical synthesis, is employed with regard to the remaining disclosure.

In order to investigate the chemotherapeutic effect of the tripeptide compound, various in vitro and in vivo analyses utilizing a variety of different origins and etiologies, as well as, primary human ALL, AMML and Hairy cell leukemias.

In order to determine the length of exposure to the tripeptide compound necessary to induce cytopathology and cytolysis, tumor cells were treated for periods ranging from 15 minutes to several hours.

The in vitro analysis of the cytolytic potential of the tripeptide compound was carried out using well characterized rodent, primate, and human tumor cell models. The first series of experiments investigated the dosage and the length of exposure to the tripeptide compound necessary to induce irreversible cytopathology or morphological alternations of the neoplastic cells. The viabilities of each of the seven in vitro tumor cells tested was significantly reduced by the treatment from 1 to 24 hours, with 1 to 50 µg of the tripeptide compound per ml of solvent carrier. Under identical treatment conditions, freshly isolated human leukemic cells, particularly all lymphoblast cells, were more susceptible to the tripeptide compound than any of the other tumor cell models. Prolonged exposure of the tumor cells to the tripeptide compound increased the rate of tumor cell death.

In view of the broad spectrum of in vitro therapeutic activity of the tripeptide compound against tumor cells, a study was initiated to determine the in vivo therapeutic activity. There is considerable evidence that leukemia in AKR mice mimics human leukemias in many respects, and it is probable that AKR mice leukemia is analogous to human acute T-cell lymphocytic leukemia.

Tumor bearing mice were treated with a single dose of 10, 15, or 20 mg of the tripeptide compound per kg of rodent weight. The results clearly demonstrate that the tripeptide compound effectively reduced the tumor burden with an increase in the mean survival time (MST) from 8 to 30 days and the "cure" of 30% of the treated mice. It is also important and significant that the tripeptide compound provide good sustainment of remission as indicated by the fact that 30% of the treated animals were alive 80 days after treatment.

The following description will more fully describe the chemotherapeutic effect of the tripeptide compound.

(Therapy A; ■), and 5 mg/kg on days 1, 4, 6, 21, and 42 (Therapy B; ▲).

Figure 7:
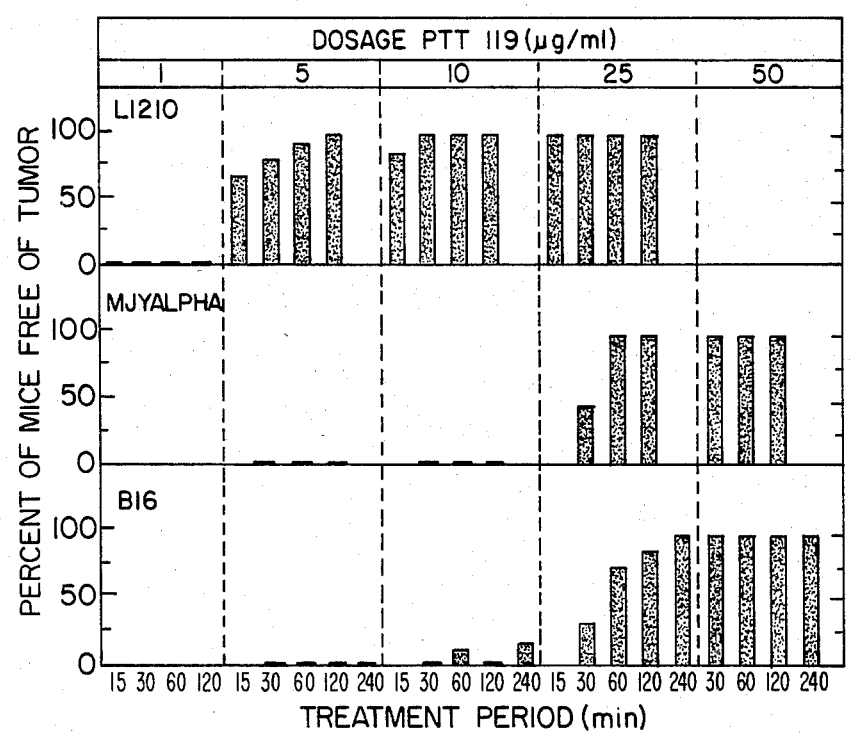

FIG. 7 shows in vivo tumorigenicity of L-1210 leukemia, MJY-alpha mammary tumor, and B-16 melanoma treated with 1 to 50 μg of the tripeptide/ml. Tumor cells were treated for 15 min to 4 hr, washed and grafted into syngeneic hosts at a concentration of $1 \times 10^6$.

Figure 8:
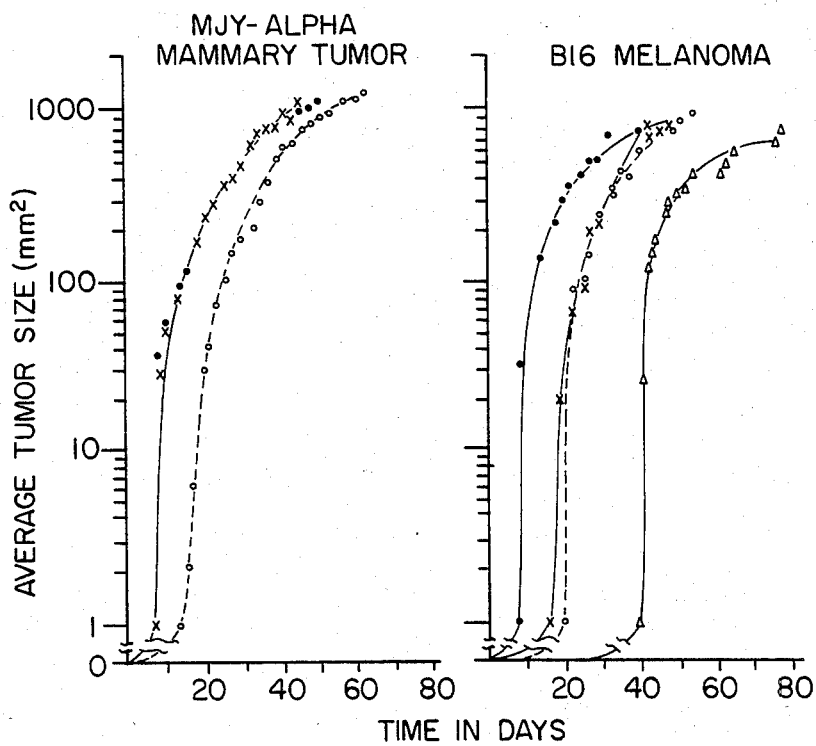

FIG. 8 shows average tumor size of MJY-alpha mammary tumor cells or B-16 melanoma implanted into BALB/c and C57BL/6 mice, respectively as a function of time after implantation. Tumor cells were treated for 2 hrs with 0 (●—●), 5 (x—x), 10 (o—o), 25 (Δ—Δ), and 50 (□—□) μg of tripeptide/ml, washed and grafted at $10^6$ cells s.c. The readings are averages obtained from 2 experiments with a total of 25 to 40 animals per group.

Figure 9:
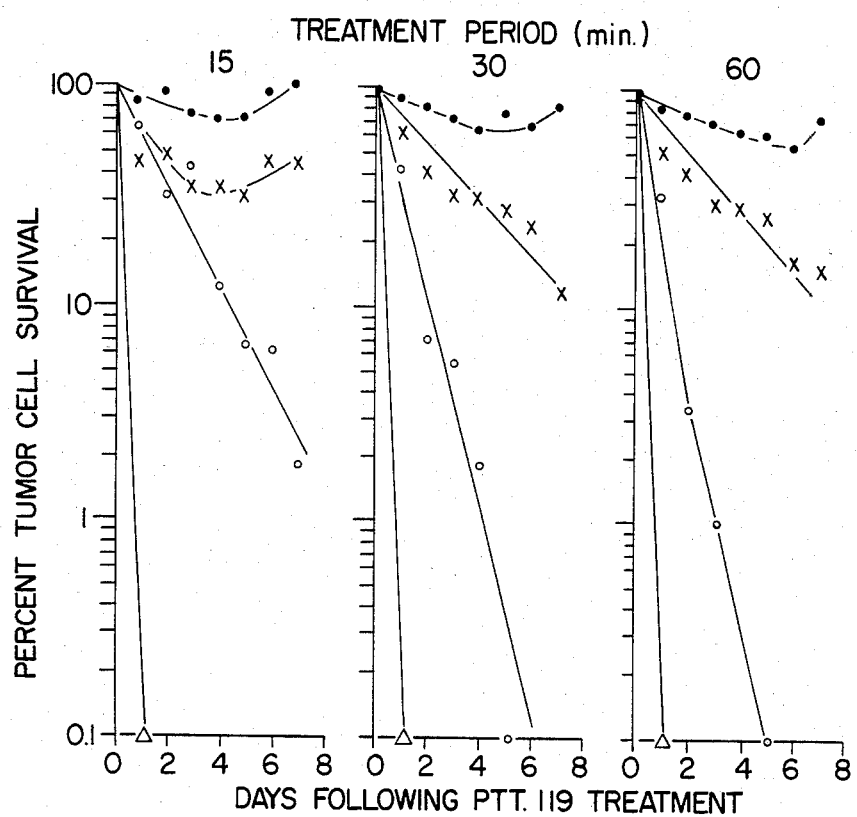

FIG. 9 shows survival of L-1210 leukemia cells following 15, 30 and 60 min treatment with 1 (●—●), 5 (x—x), 10 (o—o), 25 (Δ—Δ) μg of tripeptide/ml. L-1210 cell suspensions contained $1 \times 10^6$ cells at the time of treatment. Viability was determined for 7 days and the data represent the average of duplicate samples from 2 experiments.

Figure 10:
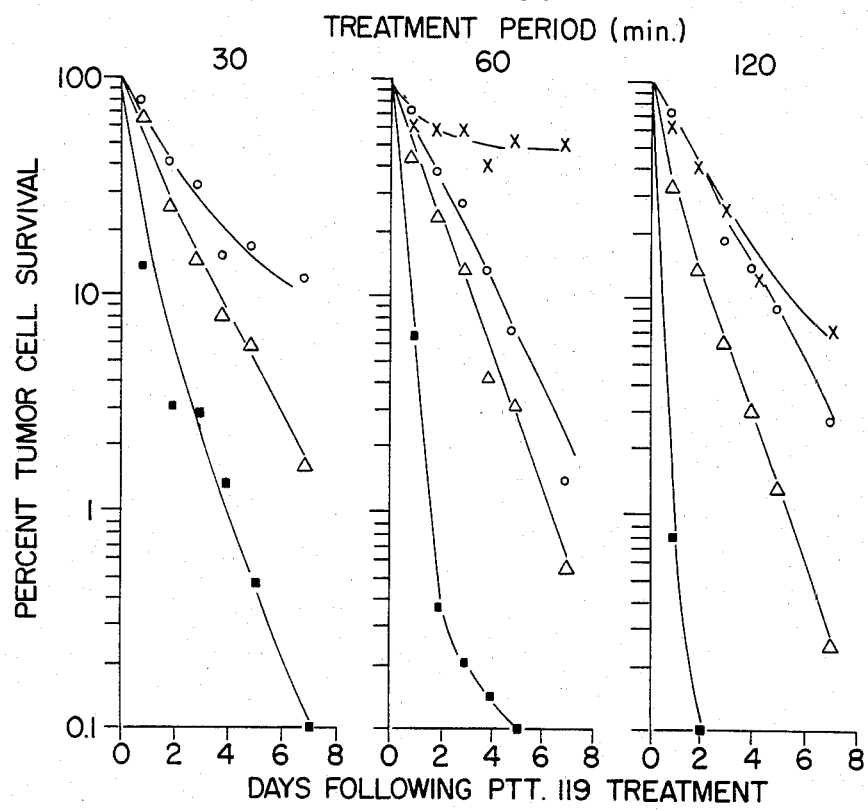

FIG. 10 shows survival of MJY-alpha mammary tumor cells following 30, 60 and 120 min exposure to the tripeptide concentrations of 5 (x—x), 10 (o—o), 25 (Δ—Δ), and 50 (■—■) μg/ml. Cells were treated at $1 \times 10^6$ cells/ml and were then seeded at $2 \times 10^5$ cells/2 2 cm² following washing. Viability was monitored daily for 7 days. The data represent the average of duplicate samples from 3 experiments.

Figure 11:
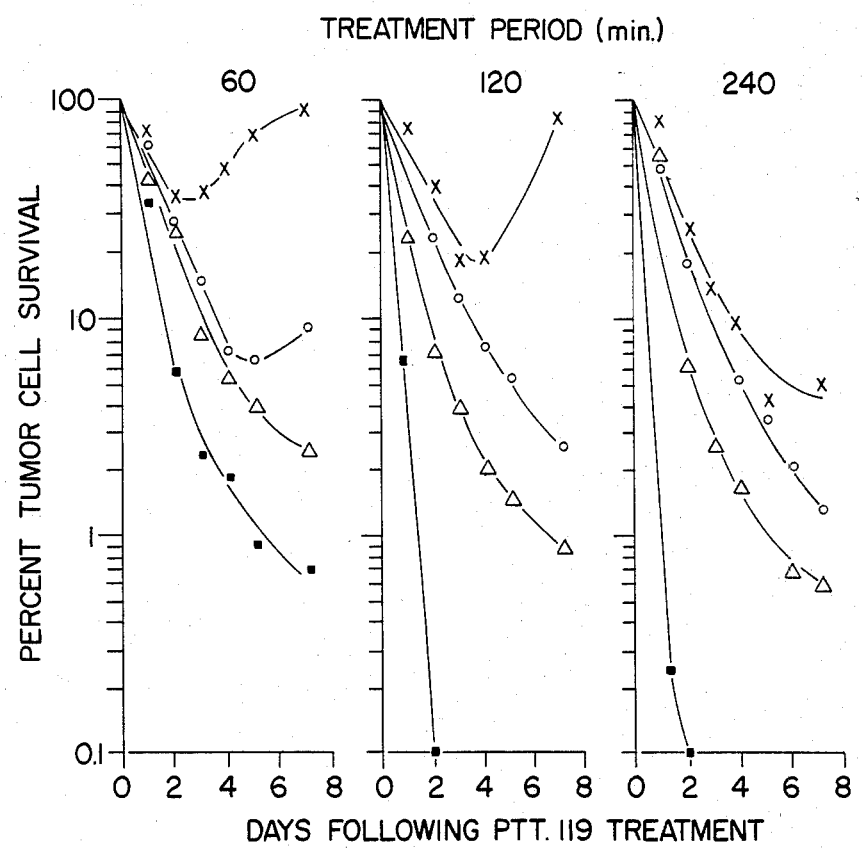

FIG. 11 shows survival of B-16 melanoma cells following 60, 120 and 240 min exposure to 5 (x—x), 10 (o—o), 25 (Δ—Δ), and 50 (■—■) μg of tripeptide/ml. B-16 cells were treated at a concentration of $6 \times 10^5$, washed, seeded at $2.2 \times 10^5$ cells/2 cm² and viability determined for 7 days. Data represent the average of duplicate samples from 3 experiments.

DETAILED DESCRIPTION OF THE EMBODIMENTS

In Vitro Preparation

The preparation for the in vitro analysis of the tumor cells is as follows: The murine mammary tumor cell line, MJY-alpha, was derived from adenocarcinomas induced in BALB/cf3H females as a result of infection and oncogenesis by the mouse mammary tumor virus (MMTV). The epithelioid cell line was tumorigenic in syngenic BALB/c hosts and was used between the 25th and 65th in vitro subcultures. Growth medium was RPMI medium No. 1640 supplemented with 18% fetal calf serum, 10 mM bovine insulin, penicillin (250 U/ml) and streptomycin (100 μg/ml).

B-16 melanoma cell cultures were established from the transplantable B-16 tumor line passaged subcutaneously in male, C57BL/6Jx mice. Melanomas from 3 to 5 mice were finely minced, washed three times with serum-free growth medium and cultured as explants using Minimal Essential Medium containing D-valine and Earle's compounds supplemented with 20% calf serum and antibiotics. Confluent primary explant cultures were subsequently passaged weekly as single cell suspensions using a solution of STV. Two, 4 to 12 month old B-16 cell cultures initiated in this manner were used between their 13th to 45th in vitro passages. Both in vitro lines of B-16 cells contained melanized cells and were tumorigenic in syngenic mice.

Primary L-1210 leukemia suspension cultures were initiated from the virulent, in vivo ascites line maintained in DBA/2 Ba mice or their $F_1$ hybrid, $BDf_1$ (BALB/cxDBA/2). L-1210 cells were harvested by washing the peritoneal cavity of tumor-bearing mice with physiological saline (0.85% NaCl, pH 7.2) containing 5% heparin (v/v) without preservatives. Leukemic cells were separated on Ficoll-Hypaque gradients followed by several washes in 0.01M phosphate-buffered saline, pH 7.4. Tumor cell preparations were consistently free of erythrocytes, and 98% of the L-1210 cell population excluded trypan blue. Suspension cultures were initiated and maintained in RPMI medium No. 1630 containing 10% fetal calf serum and antibiotics.

The Epstein Barr Virus infected human, B-lymphoma cell lines; Raji and $P_3HR$-1 were cultured as suspensions in RPMI medium No. 1640 supplemented with 10% heat inactivated fetal calf serum, penicillin (250 U/ml) and streptomycin (250 μg/ml). Culture densities were adjusted to $5$–$10 \times 10^5$ cells/ml and media replenished twice a week.

The 5-78 T cell rabbit (AACR strain) lymphoma, and the EBV-infected B lymphoma B95-8 from marmosets were also maintained as suspension cultures. Their growth conditions were similar to that used for culture of the human lymphoma cell lines.

Human AMML, ALL and Hairy cell leukemia were obtained from untreated patients undergoing leukophoresis prior to chemotherapy. Leukemic cells were separated on Ficoll-Hypaque gradients and processed as outlined for L-1210 cells.

All cultures were incubated at 37° C. in a humidified atmosphere of 5% $CO_2$ in air. Media, culture fluids and cell suspension were routinely checked for bacterial and fungal contaminations by use of tryptose phosphate broth; cultures were also checked for mycoplasma contamination by the method of Todaro et al.

Preparation of the Chemotherapeutic Agent

The tripeptide compound 3-(p-fluorophenyl)-L-alanyl-3-[m-bis(2-chloroethyl)aminophenyl]-L-alanyl-L-methionine ethyl ester hydrochloride) was initially dissolved at a concentration of 10 mg per ml of a solution of 0.25 ml of N,N-dimethylacetamide, 0.25 ml of absolute ethanol and 0.5 ml of propylene glycol. In the solvent solution, the absolute ethanol can be replaced with Tween 80 or other physiological and pharmaceutical emulsifiers. Stock solutions of one or two mg per ml were prepared by further dilution in an aqueous solution of 50% propylene glycol just prior to use. Aliquots of all stock solutions were added directly to the culture media to obtain a final concentration of 0.1–50 μg/ml. Controlled cultures treated with diluent received the identical volume of stock solution without the chemotherapeutic agent.

Treatment of MJY-Alpha and B-16 Cell Layers

MJY-alpha mammary tumor cell layers were initiated at $2 \times 10^5$ cells/2 cm² well (Nuncion Multidish 4, Vangard International, Neptune, NJ) using cells spontaneously released into the medium from confluent 6–8 day old cell layers. B-16 melanoma cells obtained from 4-day-old cell confluent cultures by trypsinization with STV were plated at $2.2 \times 10^5$ cells/cm² well. These seeding densities yielded lightly confluent layers (2.3–2.6 $\times 10^5$ cells/cm²) within 24 hr. One day after subculture, the cell layers were rinsed with media and then treated with either media with no additives, or media containing the tripeptide, at concentrations ranging from 1 to 50 μg/ml media. Treatment periods ranged from 15 min to 24 hr at 37° C. Following treatment the layers were rinsed twice and reincubated with growth media: media were changed daily until the cultures were terminated.

Treatment of Lymphoid Cell Lines and Human Leukemias

All rabbit, marmoset and human lymphoid in vitro cell lines, murine L-1210 leukemia and primary human leukemias were treated at cell concentrations of 6–10×10$^5$ cells/ml. The tripeptide was added to the cell suspensions to yield final concentrations of 1 to 50 μg/ml. Cultures were treated at 37° C. for periods ranging between 15 min to 24 hr. Following treatment, aliquots were removed and centrifuged at 800 rpm for 9 min, at 5° C. Treatment media were gently aspirated and the lymphoid cells resuspended in fresh growth media and reincubated at 37° C. Culture media were changed daily by gently pelleting the cells and exchanging 60–70% of the spent supernatant with fresh media.

Tumor Cell Survival

Survival of tumor cell layers or suspensions was ascertained using 0.5% trypan blue in 0.1M phosphate-buffered saline, pH 7.25. Cell layers were released from the Multidish-4 wells with 0.5 ml STV, diluted 2 to 10 fold with the vital strain; tumor cells in suspension cultures were directly mixed 1:1 with the trypan blue dye. Tumor cells were enumerated using a haemocytometer; all 10 fields were counted for every sample. Percent viable cells was determined by direct comparison of the numbers of cells excluding trypan blue in treated cultures to those in untreated or diluent-treated parallel cultures. There were no significant differences in the viability of cells treated with diluent when compared to untreated cells.

EXPERIMENTAL EXAMPLE 1

The ability of the tripeptide compound to inhibit the growth and survival of neoplastic cells was first assessed using the MJY-alpha mammary tumor cell line and the transplantable L-1210 leukemia. The numbers of viable cells in in vitro MJY-alpha cell layers and L-1210 cell suspensions were determined following continuous 24 hr. exposure to 0.1 to 50 μg of the tripeptide compound per ml. Significant decreases in mammary tumor (46–80%) and leukemia cells (18–94%) survival were observed at all concentrations of the tripeptide compound tested including dosages less than 10 μg/ml (Table 1). The results reveal that the cancericidal activity of the tripeptide compound resulted from the direct interaction of the drug with the tumor cells and that it did not require metabolic conversion by the animal hosts for activation.

TABLE 1
CYTOTOXIC EFFICACY OF THE TRIPEPTIDE compound AND PARENTAL COMPONENTS
L-1210 leukemia cell suspensions (1 × 10$^6$ cells/ml) and MJY-alpha mammary tumor cell layers (2.5 × 10$^5$ cells/cm$^2$) were treated for 24 hr and the percentage of viable cells compared to untreated cells and control cells receiving diluent.
Percent Tumor Cell Survival

| L-1210 Leukemia ug of Tripeptide compound/ml | | | | | MJY-Alpha Mammary Tumor ug of Tripeptide compound/ml | | | | |
|---|---|---|---|---|---|---|---|---|---|
| 0.1 | 1 | 5 | 10 | 25 | 1 | 5 | 10 | 25 | 50 |
| 82 | 70 | 62 | 28 | 6 | 54 | 41 | 36 | 27 | 20 |

EXPERIMENTAL EXAMPLE 2

In order to establish the in vitro spectrum of the cancericidal activity of the tripeptide compound against various cell types, leukemias of B and T cell origins, melanoma and mammary tumor cell lines were subjected to continuous tripeptide compound treatment. Loss of cellular viability was observed in all tumor cell lines following 24 hr exposure to the tripeptide compound (Table 2). Decreases in tumor cell survival were observed at all doses, and the sensitivity of each tumor cell line was dose dependent between the concentrations of 1 to 50 μg of tripeptide compound/ml. Comparison of the leukemia, melanoma, and mammary cancer cell types revealed that they were differentially susceptible to the tripeptide compound induced cytotoxicity at any given concentration of the tripeptide compound. Leukemia cells were usually more susceptible to the cancericidal action of the tripeptide compound and cellular toxicity was observed within the first 4 hrs of exposure. However, appreciable decreases in mammary tumor and melanoma cell survivals were detected only after 8 hrs of treatment with the tripeptide compound.

The tripeptide treatment of the murine mammary tumor cell lines, MJY-alpha, not only reduced tumor cell survival in a dose-dependent manner but also decreased the production of extra cellular mouse mammary tumor virus (MMTV). Replication of this B-type retrovirus was reduced by 27% when MJY-alpha cells were exposed to 10 microgram of the tripeptide/ml for zero to 25 hours; continuous treatment for another 24 hours further reduced MMTV production by 82%. These decreases could not be accounted for by the degree of the tripeptide induced sytolysis; tumor cell survival was reduced by only 8% and 25%, respectively, during these time periods.

In order to unravel the antimetabolic activity of the tripeptide, we carried out several experiments to ascertain the effects of the compound on viral replication. Our previously described studies assessing the cancericidal activity of the tripeptide in nine tumor cell lines (Table 2) indicated that in addition to the increased sensitivity of lymphoma-leukemia cells to the agent, cells infected with and producing RNA or DNA viruses were generally more sensitive. Examination of the cellular metabolism using radio-labeled nucleic and amino acids demonstrated that the antiviral activity was not the result of blockage in cellular uptake and incorporation of precursors.

Utilizing *isotopically-labeled uridine*, a significant decrease was detected in the production of the RNA tumor virus MMTV by the MJY-alpha mammary tumor cells. Viral replication was reduced by 42% when cells were treated with 10 μg of the tripeptide at the time of labeling. Cultures treated with this concentration 24 hours following radiolabeling of the cells also produced 37% less MMTV compared to controls, indicating that antiviral activity was not merely the result of a cellular blockage in the uptake of precursors.

The structural proteins on MMTV virions purified from cultures treated with the tripeptide were analyzed in order to determine if the tripeptide induced any biochemical changes in the particles. Profiles of MMTV glycol proteins and non-glycosylated polypeptides obtained by sodium dodecyl-sulfate polyacrylamide gel electrophoresis revealed a specific 60 to 78% decrease in the major non-glycosylated core protein, P24. The relative levels of the other MMTV polypeptides were not affected.

treatment; the surviving fractions ranged from 0 to 100% in a dose dependent manner. Similar levels of cell death were never immediately observed in any of the tumor cell models at these concentrations. The cancericidal activity of the tripeptide compound was also greater against uncultured human tumor cells than any of the tumor cell lines after 24 hrs of treatment.

TABLE 2
SUSCEPTIBILITY OF TUMOR CELL LINES TO CONTINUOUS EXPOSURE TO THE TRIPEPTIDE SALT
Tumor cell layers and suspensions were exposed to 1 to 50 ug of the tripeptide salt per ml for 24 hr. Viability was determined after 1, 4, 8 and 24 hr of treatment. Results are the average of duplicate samples of at least three separate experiments.

| Cell Line | Cell Type | Virus Type | Virus Production | Tripeptide ug/ml | % tumor cell survival exposure (hr) 1 | 4 | 8 | 24 |
|---|---|---|---|---|---|---|---|---|
| Mouse | | | | | | | | |
| L-1210 | Leukemia | MuLV | + | 1 | 95 | ND | 100 | 65 |
| | | | | 5 | 100 | 84 | ND | 57 |
| | | | | 10 | 92 | 75 | ND | 12 |
| | | | | 25 | 50 | 25 | 15 | 0 |
| B-16 | Melanoma | — | — | 5 | 100 | 100 | 100 | 74 |
| | | | | 10 | 100 | 100 | 63 | 64 |
| | | | | 25 | 100 | 100 | 92 | 60 |
| | | | | 50 | 100 | 100 | 58 | 33 |
| MJY-alpha | Mammary Tumor | MMTV | ++ | 5 | 100 | 100 | 100 | 53 |
| | | | | 10 | 100 | 100 | 100 | 33 |
| | | | | 25 | 100 | 100 | 98 | 25 |
| | | | | 50 | 98 | 87 | 62 | 19 |
| Rabbit | | | | | | | | |
| 5-78 | T-lymphoma | HVA | + | 5 | 100 | 88 | ND | 66 |
| | | | | 10 | 89 | 61 | ND | 49 |
| | | | | 25 | 75 | 32 | 14 | 6 |
| | | | | 50 | 57 | 4 | ND | 2 |
| Marmorset | | | | | | | | |
| B95-8 | B-lymphoma | EBV | + | 10 | 100 | 100 | ND | 40 |
| | | | | 25 | 100 | 86 | 49 | 20 |
| | | | | 50 | 77 | 42 | 26 | 6 |
| Human | | | | | | | | |
| Raji | B-lymphoma | EBV | — | 10 | 98 | 98 | ND | 82 |
| | | | | 25 | 100 | 97 | 97 | 35 |
| | | | | 50 | 94 | 90 | 76 | 20 |
| P HR-1 | B-lymphoma | EBV | + | 10 | 96 | 91 | ND | 75 |
| | | | | 25 | 92 | 86 | ND | 69 |
| | | | | 50 | 93 | 75 | ND | 60 |

1. MuLV = murine leukemia virus; MMTV = mouse mammary tumor virus; HVA = herpes-virus ateles; EBV = Epstein-Barr virus.
2. ND = Not Done

TABLE 3
EFFICACY OF THE TRIPEPTIDE SALT AGAINST HUMAN CELLS
Human leukemic cells obtained by leukophoresis from untreated patients were treated with 1 to 50 ug of the tripeptide salt for 24 hr. Tumor cell viability was determined on duplicate samples following 1, 4, and 24 hr exposure.

| | Tripeptide (ug/ml) | Exposure (hr) 1 | 4 | 24 |
|---|---|---|---|---|
| Hairy cell leukemia | 5 | 100 | 80 | 34 |
| | 10 | 100 | 71 | 81 |
| | 25 | 92 | 71 | 12 |
| | 50 | 37 | 21 | 7 |
| AMML | 1 | 95 | 85 | 66 |
| | 5 | 50 | 52 | 66 |
| | 10 | 60 | 41 | 21 |
| | 25 | 20 | 15 | 14 |
| | 50 | 4 | 3 | 4 |
| ALL (N cell leukemia) | 1 | 98 | 76 | 25 |
| | 5 | 46 | 29 | 7 |
| | 10 | 32 | 15 | 0 |
| | 25 | 15 | 15 | 0 |

EXPERIMENTAL EXAMPLE 3

Leukemic cells obtained by leukophoresis from untreated patients with Hairy cell, AMML, and ALL leukemias were continuously treated with the tripeptide compound (Table 3). Lymphoblast from a patient with ALL leukemia were particularly sensitive to the tripeptide compound; cell survival was reduced by 75% following treatment with as low as 1 μg of the tripeptide compound. AMML and Hairy cell leukemias were also sensitive to all concentrations of the tripeptide compound; the numbers of viable cells were reduced by 34% to 96% after 24 hr treatment. It is noteworthy that cytotoxicity was detected in the fresh leukemia preparations within the first hour of the tripeptide compound

TABLE 3-continued
EFFICACY OF THE TRIPEPTIDE SALT AGAINST HUMAN CELLS

Human leukemic cells obtained by leukophoresis from untreated patients were treated with 1 to 50 ug of the tripeptide salt for 24 hr. Tumor cell viability was determined on duplicate samples following 1, 4, and 24 hr exposure.

| Concentration Tripeptide (ug/ml) | % Tumor cell survival Exposure (hr) | | |
|---|---|---|---|
| | 1 | 4 | 24 |
| 50 | 0 | 0 | 0 |

EXPERIMENTAL EXAMPLE 4

Several of the tumor cell models and the primary human leukemias displayed tripeptide compound induced cytotoxicity within 1 to 4 hours of exposure to the tripeptide compound indicating that continuous 24 hr treatment may not be required for the reduction of the tumor cell populations. To delineate the minimum concentration and duration of the tripeptide compound exposure to induce cytolysis, MJY-alpha and B-16 melanoma cell layers and L-1210 leukemia cell suspensions were exposed to 0.5 to 50 μg of the tripeptide compound per ml of solvent for 0.25 to 4 hours. The tripeptide compound was then removed and the cells washed and reincubated in media growth. Tumor cell viability was determined 24 hrs after pulse tripeptide compound exposure. Cell survival of all three tumor cell lines was reduced by an exposure period of as short as 15 min (Table 4). The degree of cytolysis increased with extension of the treatment periods from 15 min to 4 hrs, although the decreases in cell survival were not proportional to the duration of the exposure. However, a concentration dependent decrease in cell survival was observed in the three murine tumor models for each treatment period. Comparison of the data in Tables 2 and 4 reveal that cells exposed to the tripeptide compound for one hour were irreversibly damaged when assayed a day later despite their apparent viability immediately after treatment. Of greater importance was the demonstration that pulse exposure to any concentration of the tripeptide compound was almost as effective as continuous 24 hr treatment in reducing the number of tumor cells.

TABLE 4
SUSCEPTIBILITY OF TUMOR CELLS TO PULSE-TREATMENT WITH THE TRIPEPTIDE SALT

MJY-alpha mammary tumor and B-16 melanoma cell layers and L-1210 leukemia cell suspensions were pulse-treated with the tripeptide salt, washed with media and their viability determined 24 hr later. Values are the average of duplicate samples from four experiments.

| Cell Line | Tripeptide | Percent Tumor Cell Survival Treatment Period (hr) | | | | |
|---|---|---|---|---|---|---|
| | | .25 | .5 | 1 | 2 | 4 |
| MJY-alpha | 5 | ND[1] | 94 | 89 | 77 | 76 |
| | 10 | 68 | 67 | 70 | 64 | 48 |
| | 25 | 61 | 37 | 51 | 46 | 44 |
| | 50 | 45 | 32 | 41 | ND | ND |
| B-16 Melanoma | 5 | ND | 93 | 88 | 66 | 79 |
| | 10 | ND | 75 | 68 | 73 | 63 |
| | 25 | 82 | 67 | 60 | 56 | 52 |
| | 50 | 65 | 62 | 48 | ND | ND |
| L-1210 Leukemia | .5 | 95 | 90 | 83 | 94 | 68 |
| | 1 | 80 | 87 | 83 | 78 | 45 |
| | 5 | 72 | 60 | 61 | 57 | 35 |
| | 10 | 53 | 40 | 27 | 31 | 37 |
| | 25 | 20 | 7 | 0 | 0 | 0 |
| | 50 | 0 | 0 | 0 | ND | ND |

[1]ND - Not Done

EXPERIMENTAL EXAMPLE 5

Figure 1:
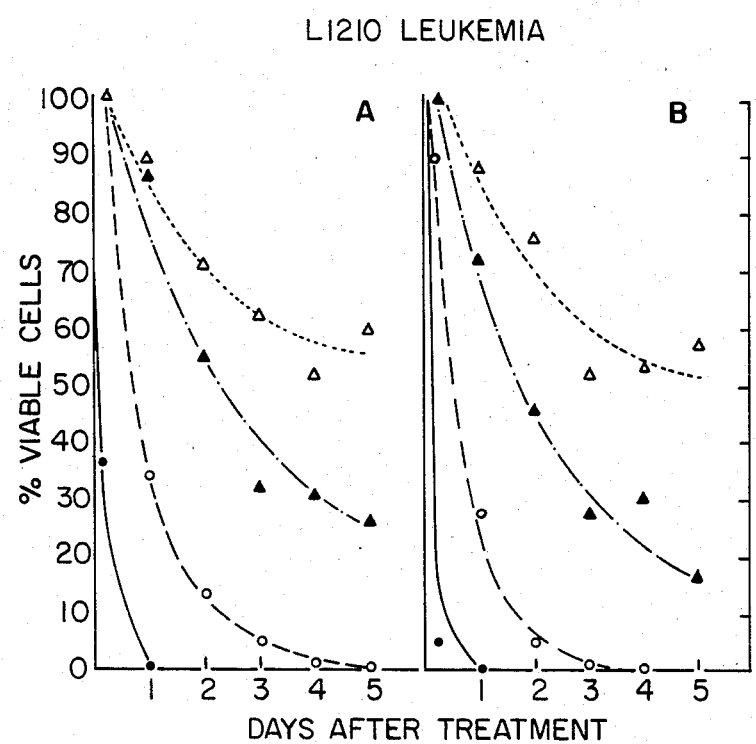
FIG. 1 shows survival of L-1210 leukemia suspensions following a 30 min (A) or 1 hr (B) pulse exposure to 1 (Δ·Δ), 5 (▲—▲), 10 (o—o) and 25 (●—●) µg of the tripeptide/ml of carrier solvent. L-1210 cell suspensions contained $6 \times 10^5$ cells/ml at the time of treatment and the range of viable control cells during the 5-day observation period was $6.5-10 \times 10^5$ cells/ml.
Figure 2:
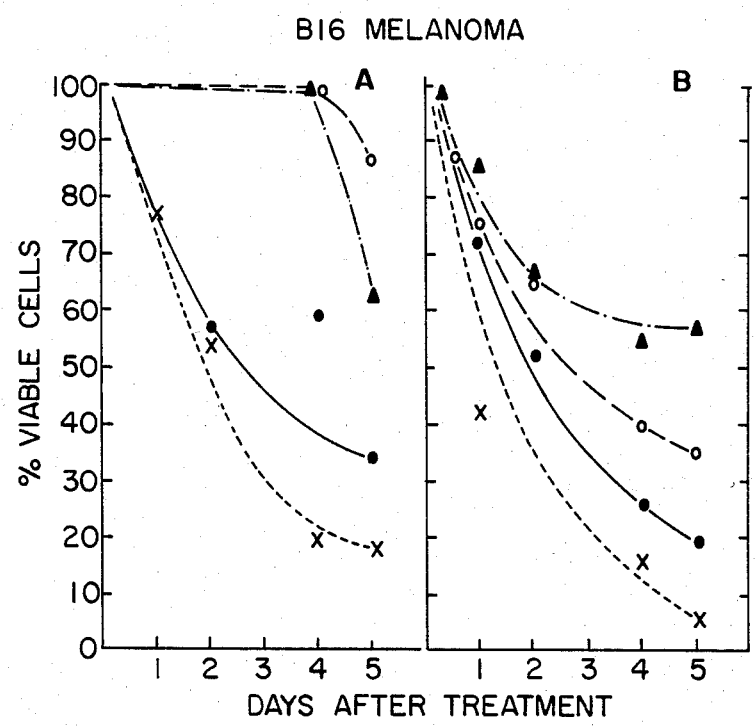
FIG. 2 shows survival of B-16 melanoma cell layers following 30 min (A) or 1 hr (B) pulse treatment with 5 (▲——▲), 10 (o—o), 25 (●—●), and 50 (X—X) µg of the tripeptide ml of carrier solvent. The numbers of cells in the 24-hr-old layers at the time of treatment were $2.7-3 \times 10^5$ B-16 melanoma cells per well. The ranges of viable control cell numbers during the 5-day observation period were $3.5-12 \times 10^5$ MJY-alpha cells and $1.5-4 \times 10^5$ B-16 cells per well.
Figure 3:
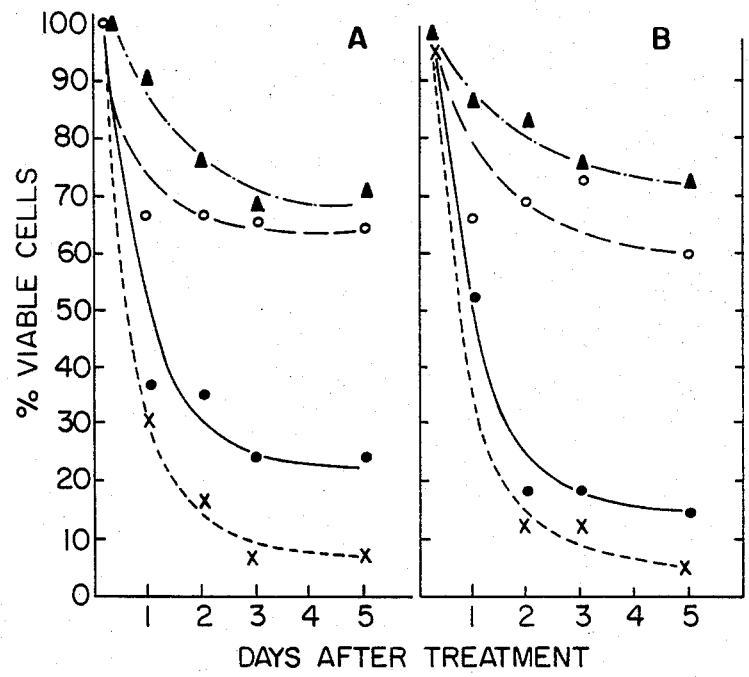
FIG. 3 shows survival of MJY-alpha mammary tumor cells following 30 min (A) or 1 hr (B) pulse treatment with 5 (▲——▲), 10 (o—o), 25 (●—●) and 50 (X—X) µg of the tripeptide/ml of carrier solvent. The numbers of cells in the 24-hr-old layers at the time of treatment were $2.9-3.2 \times 10^5$ MJY-alpha cells. The ranges of viable control cell numbers during the 5-day observation period were $3.5-12 \times 10^5$ MJY-alpha cells.

Pulse treatment of mammary, melanoma and leukemia tumor cells with the tripeptide compound reduced the number of viable cells 24 hrs after exposure. In order to ascertain if the remaining cells were resistant to the tripeptide compound and be able to replicate and repopulate the culture vessels, longitudinal assessments of the surviving cell fractions were made. MJY-alpha mammary tumor and B-16 melanoma cell layers, and L-1210 leukemia cell suspensions were treated with 1 to 50 μg of the tripeptide compound per ml for 30 min or 1 hr. Cell viabilities were determined over 5 days (FIGS. 1-3). In all three tumor systems, cell viabilities decreased over the examination period indicating that the population was irreversibly affected by pulse exposure to tripeptide compound. The degrees and rates of tumor cell susceptibility were dependent on the tumor cell system, as well as, on the concentration and duration of the tripeptide compound exposure. Of the three tumor models, the L-1210 leukemia was the most susceptible; at any given concentration of the tripeptide compound, approximately 5 times more L-1210 cells were destroyed compared to mammary tumor and melanoma cells.

Unlike either the L-1210 leukemia and B-16 melanoma cultures which showed a gradual progression of cell cytotoxicity with increasing dosages, there was a distinct separation of cell viability between 10 and 25 μg/ml in MJY-alpha mammary tumor cells (FIG. 3). Whether this reflected a critical threshold level of the tripeptide compound for this cell line or demarcated two populations of susceptible cells is not known. In all three tumor systems, extension of the treatment period from 0.5 to 1 hour usually resulted in a more rapid rate of cell death during the first 2 to 3 days following exposure, but did not necessarily effect the total numbers of viable cells remaining on days 4 and 5. It is also significant that the cancericidal activity of the tripeptide compound was more pronounced against fresh, human ALL, AMML and Hairy cell leukemias than established tumor cell lines of murine, rabbit, primate and human origins.

IN VIVO PREPARATION

EXPERIMENTAL EXAMPLE 6

Figure 4:
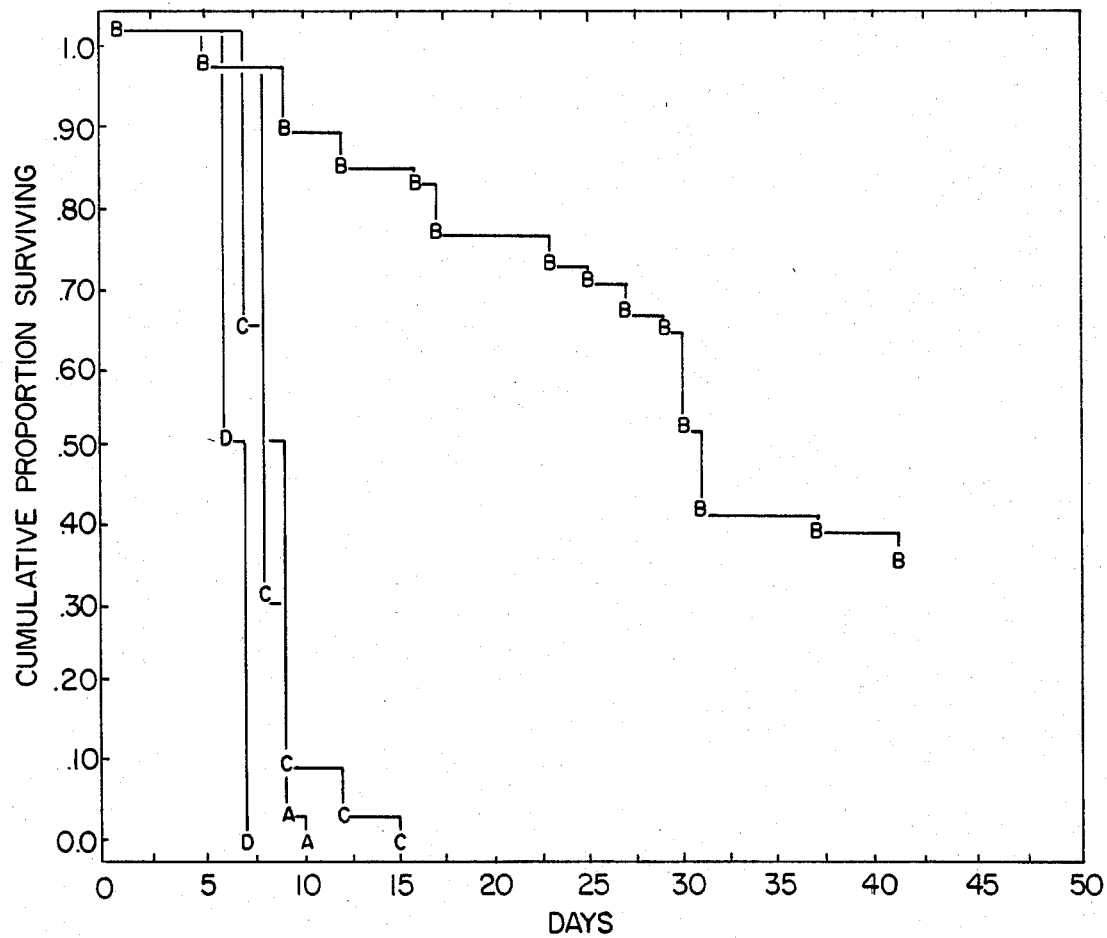
FIG. 4 shows DBA/2 mice inoculated intraperitoneally with $10^6$ L-1210 leukemia cells on Day 0. (A) Control animals. Mice were treated on Day 2 with the tripeptide at (B) 10 mg/kg of rodent weight; (C) 15 mg/kg; and (D) 20 mg/kg.

In view of the broad spectrum of in vitro therapeutic activity of the tripeptide compound against murine, rabbit, primate, and human tumor cell lines, an experiment was initiated to determine the in vivo therapeutic activity of the tripeptide compound. The following experiments were performed with the tripeptide compound. Male mice were inoculated intraperitoneally on day 0 with $10^6$ untreated leukemia L-1210 cells. The tumor bearing mice were treated 48 hours later with a single dose of 10, 15, and 20 mg of the tripeptide compound per kg weight of the test animal. Results clearly demonstrate the tripeptide compound effectively reduced the tumor burden with an increase of the mean survival time from 8 to 30 days (275%) and the apparent "cure" of the 30% of the treated animals. See FIG. 4.

EXPERIMENTAL EXAMPLE 7

Leukemia in AKR mice, which is the result of the oncogenic activity of the endogenous Gross leukemia virus, has been effectively used as a model for human leukemias in the studies of tumor biology, chemotherapy, and chemoimmunotherapy. There is considerable evidence that leukemia in the AKR mice mimics human leukemias in many respects, and it is probable that AKR leukemia is analogous to human acute T-cell lymphocytic leukemia. Leukemic cells first appear in the thymus of mice at 6 to 12 months of age. Controlling this disease is formidable, since the cure or long range control of spontaneous leukemia in AKR mice require the therapeutic eradication of virtually all of the oncogenic cells. The time lapse between the first appearance of viable lymphoma cells in the thymus and the clinical diagnosis is about 30 days.

Figure 5:
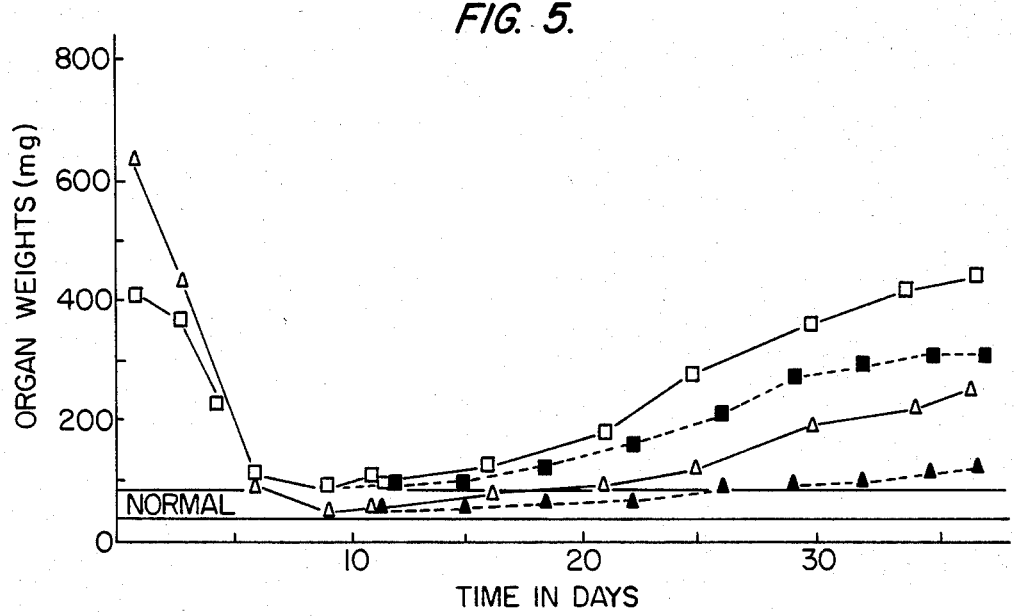
FIG. 5 shows change of organ weights after chemotherapy with the tripeptide treated AKR mice with spontaneous leukemia. Chemotherapy consisted of: Group A: 10 mg/kg of rodent weight on days 1 and 14; Group B: 5 mg/kg on days 1, 4, 7, 21, and 42. At designated intervals 4 mice from each experimental group were selected at random, sacrificed and their spleen and thymus weights determined. Group A: Mean thymus wt (Δ—Δ); Mean spleen wt (□—□) Group B: Means thymus wt (▲—▲); Mean spleen wt (■—■).
Figure 6:
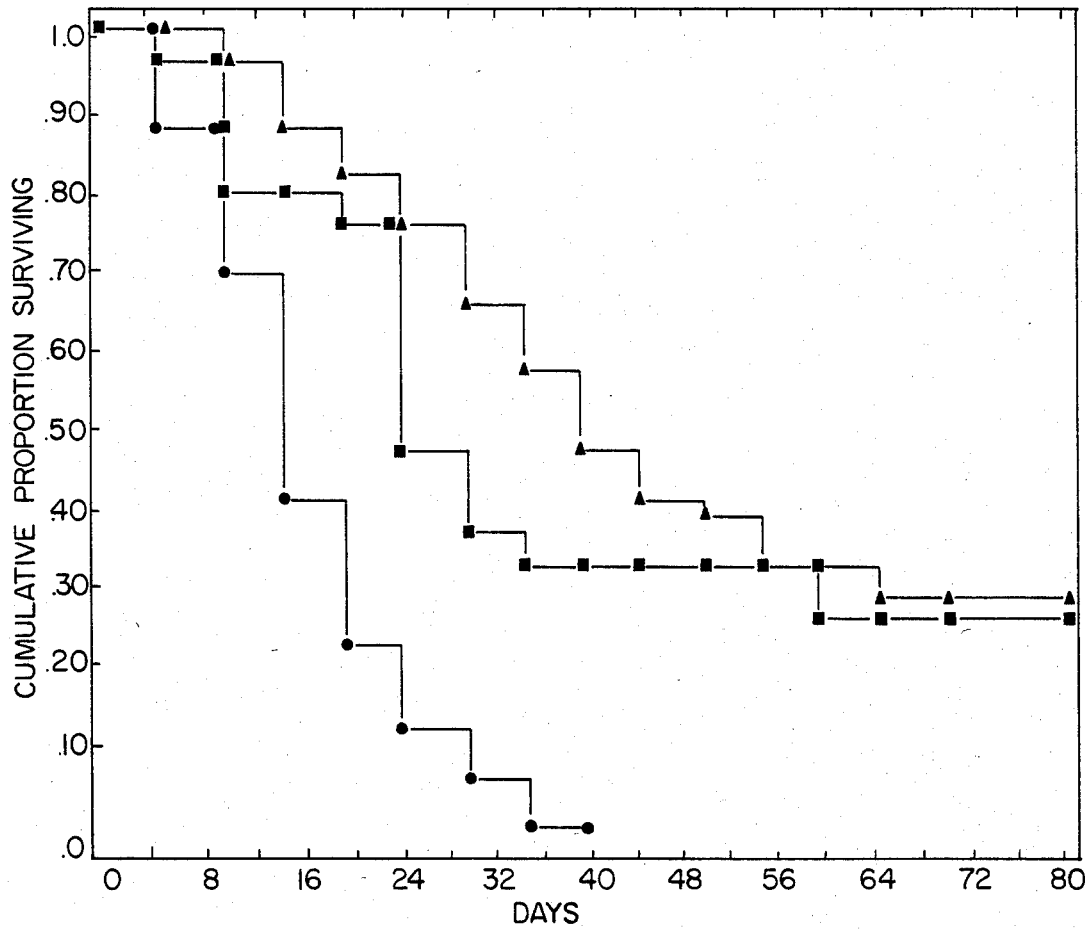
FIG. 6 shows AKR mice with spontaneous leukemia. Control mice (o); mice received intraperitoneal injections of the tripeptide at 10 mg/kg on days 1 and 14

The effectiveness of the tripeptide compound in the treatment of spontaneous leukemia in AKR mice was tested. The clinical diagnosis of spontaneous leukemia in AKR mice was made with 95% accuracy by splenic and lymph node palpation, followed by leukocyte count. There is good evidence that at the time of clinical diagnosis there are $0.6\text{--}1.8 \times 10^9$ widely disseminated lymphoma cells in AKR mice. Without cytoreductive therapy, AKR mice die after diagnosis of spontaneous leukemia at the rate of 50% by 14 days, 90% by 33 days, and 96% by 56 days. In the preliminary experiment using AKR mice with spontaneous leukemia, good remission induction was achieved with the tripeptide compound administered either at 10 mg per kg weight of test animal on days 1 and 14, or at 5 mg of the tripeptide compound per kg of the test animal on days 1, 4, 7, 21, and 42. Significant reductions in leukemic thymus and spleen weights were observed after chemotherapy (FIG. 5). Reduction of thymus and spleen weights to normal is indicative of eradication of the primary tumor. Leukemic AKR mice receiving either treatment sustained a mean survival time of 200% and 100%, respectively. It is also important and significant that the tripeptide compound treatment provides good sustainment since 30% of the treated animals in either group were alive after the onset on the therapy (FIG. 6).

EXPERIMENTAL EXAMPLE 8

Data presented in FIG. 7 shows that L-1210 leukemia cells were the most susceptible to the cancericidal activity of the tripeptide. Concentrations as low as 5 and 10 μg tripeptide/ml effectively abrogated the leukemogenicity of the L-1210 cells. No tumor growth was apparent in the recipient mice receiving L-1210 cells treated with 5 μg for 2 hr, or 10 μg for 30 min or longer. The synthetic tripeptide effectively reduced the population of L-1210 cells capable of proliferation to 0. To ascertain if the recipients' immune responses were elicited against the tripeptide-treated leukemia cells, BDF$_1$ mice which had survived unsuccessful grafts of tripeptide-treated L-1210 leukemia cells for 45 days were challenged with a second graft of 1000 untreated L-1210 cells. There were no differences in the leukemogenesis of the L-1210 cells in these recipients and all mice, like the controls, died of tumor on days 12 and 13 demonstrating that implantation of L-1210 cells treated with tripeptide did not confer protection on the hosts to future grafts.

Loss of tumorigenicity of MJY-alpha mammary tumor and B-16 melanoma tumor cells was also apparent following tripeptide treatment (FIG. 7). In both tumor systems complete absence of tumor growth was observed in recipients of $10^6$ cells treated with tripeptide concentration of 25 μg or higher for 30 to 240 min. Exposure to the tripeptide compound reduced the viable population of MJY-alpha and B-16 tumor cells by at least 99.9% since their LD$_{100}$ doses are 100 viable cells. At lower tripeptide dosages, complete elimination of L-1210 leukemia, MJY-alpha mammary tumor and B-16 melanoma tumorigenicity were unattainable and significant extensions of the mean survival time (MST) of the recipient mice were observed (Table 5). BDF$_1$ mice receiving L-1210 leukemia cells treated with 5 μg of the tripeptide compound for 30 or 60 min had an ILS (increased life span) of 110% and 220%, respectively. Similarly, the survival of BALB/c mice implanted with $10^6$ MJY-alpha mammary tumor cells or C57BL/6 mice receiving B-16 melanoma cells treated with 5 to 25 μg tripeptide/ml were extended significantly beyond the 42 or 28 days, respectively, observed in the control hosts.

TABLE 5

Mean Survival Time (MST) of Syngeneic Recipients Of Tripeptide Treated Tumor Cells.
Tumor cells were treated with the tripeptide compound in vitro, washed and implanted subcutaneously into syngeneic hosts as described in materials and methods. Numbers of surviving animals were quantitated every two days. All values represent the average of two experiments each containing groups of 10-15 mice.

| Tumor Cell | Tripeptide (ug/ml) | Treatment Period (min) | | | | |
|---|---|---|---|---|---|---|
| | | 15 | 30 | 60 | 120 | 240 |
| L-1210 | 0 | 10 | 10 | 10 | 10 | — |
| Leukemia | 1 | 10 | 10 | 11 | 13 | — |
| | 5 | 13 | 21* | 32* | NT$^1$ | — |
| | 10 | 8 | NT | NT | NT | — |
| | 25 | NT | NT | NT | NT | — |
| MJY-alpha | 0 | — | 42 | 42 | 42 | — |
| Mammary Tumor | 5 | — | — | 52* | 43 | — |
| | 10 | — | 44 | 46 | 61* | — |
| | 25 | — | 56* | NT | NT | — |
| | 50 | — | NT | NT | NT | — |
| B-16 | 0 | — | 28 | 28 | 28 | 28 |
| Melanoma | 5 | — | — | 31 | 33* | 41* |
| | 10 | — | 35* | 35* | 35* | 45* |
| | 25 | — | 52* | 68* | 65* | NT |
| | 50 | — | NT | NT | NT | NT |

$^1$NT - no tumor
*p 0.001

EXPERIMENTAL EXAMPLE 9

Bioassay of Tumorigenicity

Suspensions of untreated and tripeptide treated MJY-alpha mammary tumor, B-16 melanoma, and L-1210 leukemia cells were adjusted to a concentration of $1 \times 10^7$ cells/ml based on the initial tumor cell concentration before the tripeptide exposure. Tumor cells were inoculated into syngeneic hosts at a concentration of $1 \times 10^6$ cells in 0.1 ml. Female BALB/c/Crgl recipients of MJY-alpha mammary tumor cells and male C57BL/6/Jx hosts receiving B16 melanoma cells were inoculated subcutaneously; BDf$_1$ mice were given intraperitoneal injections of L-1210 cells. Subcutaneous tumors were measured along their long and short axes every 1 to 3 days; tumor size is reportd as the product of the two measurements (mm$^2$). See FIG. 8. The examination periods for mice receiving L-1210, MJY-alpha and B-16 tumor grafts were 45, 80, and 85 days, respectively. All mice were autopsied at the time of death or sacrifice.

Assessment of the tumor growth rates of the subcutaneously implanted MJY-alpha mammary tumor and B-16 melanoma cells revealed that the initial lag period between inoculation of tumor cells and the appearance of palpable tumors lengthened in both solid tumor model systems with increasing dosages of tripeptide (FIG. 8). However, tripeptide did not alter tumor progression once the graft was established; tumor growth rates of untreated and tripeptide treated MJY-alpha and B-16 cells were identical and the maximum size of the tumor at the time of death of hosts remained unchanged. This suggested that the tripeptide did not alter the kinetics of tumor cell proliferation nor did it appear to select one subpopulation of tumor cells.

EXPERIMENTAL EXAMPLE 10

Sensitivity of Mice to the Tripeptide Compound

In order to assess whether the effective cancericidal concentrations of the tripeptide compound found in the bioassays were attainable in vivo, mice were given a single intraperitoneal inoculation of the tripeptide. Demonstrable tripeptide toxicity required administration of high concentrations of the synthetic tripeptide. All mice tolerated doses of 52.5 mg/m$^2$ (15 mg/kg) with no observable signs of discomfort or pathologies. BDf$_1$ males which have been previously shown to be very sensitive to alkylating agents tolerated 61.25 mg PTT.119/m$^2$ (17.5 mg/kg; LD$_{10}$), whereas, this dose increased to 74.6 mg/m$^2$ (21.3 mg/kg) in AKR females. The LD$_{50}$ of male BDf$_1$ mice was 81.6 Mg/m$^2$ (23.3 mg/kg) and 93.5 mg/m$^2$ (27 mg/kg) for female AKR mice.

EXPERIMENTAL EXAMPLE 11

In Vitro Survival of Tripeptide-Related Tumor Cells

The reversibility of the cancericidal activity of the tripeptide compounds on L-1210 leukemia, MJY-alpha mammary tumor and B-16 melanoma cells was also monitored in the nonhostile tissue culture environment. Cell suspensions of these tumor models were treated with tripeptide for 15 to 240 min, washed and either inoculated into mice or maintained as suspension (L-1210) or monolayer cultures (MJY-alpha and B-16). Reductions in tumor cells survival were negligible (0–6%) in all three tumor systems at initiation of in vitro cultures following treatment with 50 µg tripeptide/ml for as long as 4 hrs. However, significant decreases in cellular viabilities of L-1210 leukemia (FIG. 9), MJY-alpha mammary tumor (FIG. 10) and B-16 melanoma (FIG. 11) tumor cells were observed 24 hr following tripeptide exposure and for the next 6 days.

Longitudinal examination of the cultures demonstrated that cytolysis of the tumor cells continued days after tripeptide treatment and also revealed the repopulation of tumor cell cultures treated with low concentrations of the tripeptide. A step-wise gradation in cytolysis with increasing concentrations of tripeptide was observed in the in vitro survival curves of the three tumor cell systems. At any dose of tripeptide, tumor cell survival also decreased when the treatment periods were lengthened although the L-1210, MJY-alpha and B-16 cells were refractile to these duration-related changes at several concentrations of the tripeptide. These apparent refractory phases were observed at concentrations of 10 and 25 µg of tripeptide in MJY-alpha and B-16 cells and at 1 and 5 µg of tripeptide in L-1210 leukemia cultures.

What is claimed is:

1. A method of controlling human and animal tumor cells transplanted into a living animal comprising injecting the animal with a therapeutically effective amount of a tripeptide compound, said tripeptide has members selected from a group consisting of:
    (1) 3-(p-fluorophenyl)-L-alanyl-3-[m-bis(2-chloroethyl)-aminophenyl]-L-alanyl-L-methionine
    (2) 3-[m-bis(2-chloroethyl)aminophenyl]-L-alanyl-3-(p-fluorophenyl)-L-alanyl-L-methionine
    (3) 3-(p-fluorophenyl)-L-alanyl-L-methionyl-3-[m-bis(2-chloroethyl)aminophenyl]-L-alanine
    (4) 3-[m-bis(2-chloroethyl)aminophenyl]-L-alanyl-L-methionyl-3-(p-fluorophenyl)-L-alanine
    (5) L-methionyl-3-(p-fluorophenyl)-L-alanyl-3-[m-bis(2-chloroethyl)aminophenyl]-L-alanine
    (6) L-methionyl-3-[m-bis(2-chloroethyl)aminophenyl]-L-alanyl-3-(p-fluorophenyl)-L-alanine.

2. A method of controlling tumor cells as claimed in claim 1, wherein the tripeptide compound is 3-(p-fluorophenyl)-L-alanyl-3-[m-bis(2-chloroethyl)-aminophenyl]-L-alanyl-L-methionine ethyl ester hydrochloride.

3. The method of claim 2, wherein a carrier solution is prepared by first dissolving 10 mg of the tripeptide in a solution of 0.25 ml of N,N-dimethylacetamide, 0.25 ml of pure ethanol, and 0.5 ml of propylene glycol; and then further diluting with an aqueous solution of 50% propylene glycol.

4. The method of claim 2, wherein the tumor cells are controlled with a single therapeutically effective dose between about 10 to about 20 mg of the tripeptide per kg of subject weight.

5. The method of claim 2, wherein the control of the tumor cells is by in vivo treatment by intraperitoneal administration of the tripeptide.

6. The method of claim 2, wherein the tumor cells are a member selected from a group consisting of leukemia L-1210 cells, MJY-alpha mammary tumor cells and B-16 melanoma cells.

7. The method of claim 2, wherein the tumor cells are controlled with a multiple therapeutically effective dose of the tripeptide.

8. The method of claim 7, wherein the multiple dose is administered at 10 mg per kg of subject weight on days 1 and 14.

9. The method of claim 7, wherein the multiple dose is administered at 5 mg per kg of subject weight on days 1, 4, 7, 21 and 42.

10. A method of controlling tumor cells in vitro comprising administering to the tumor cells a therapeutically effective amount of a tripeptide compound, said tripeptide has members selected from a group consisting of:
    (1) 3-(p-fluorophenyl)-L-alanyl-3-[m-bis(2-chloroethyl)-aminophenyl]-L-alanyl-L-methionine
    (2) 3-[m-bis(2-chloroethyl)aminophenyl]-L-alanyl-3-(p-fluorophenyl)-L-alanyl-L-methionine
    (3) 3-(p-fluorophenyl)-L-alanyl-L-methionyl-3-[m-bis(2-chloroethyl)aminophenyl]-L-alanine (4) 3-[m-bis(2-chloroethyl)aminophenyl]-L-alanyl-L-methionyl-3-(p-fluorophenyl)-L-alanine (5) L-methionyl-3-(p-fluorophenyl)-L-alanyl-3-[m-bis(2-chloroethyl)aminophenyl]-L-alanine (6) L-methionyl-3-[m-bis(2-chloroethyl)aminophenyl]-L-alanyl-3-(p-fluorophenyl)-L-alanine.

11. A method of controlling tumor cells as claimed in claim 10, wherein the tripeptide compound is 3-(p-fluorophenyl)-L-alanyl-3-[m-bis(2-chloroethyl)aminophenyl]-L-alanyl-L-methionine ethyl ester hydrochloride.

12. A method of controlling tumor cells in vitro comprising:

dissolving 10 mg of a tripeptide compound, said tripeptide compound is 3-(p-fluorophenyl)-L-alanyl-3-[m-bis(2-chloroethyl)aminophenyl]-L-alanyl-L-methionine ethyl ester hydrochloride, in a solution of 0.25 ml of N-N-dimethylacetamide, 0.25 ml of absolute ethanol and 0.5 ml of propylene glycol; diluting the dissolved tripeptide compound in an aqueous solution of 50% propylene glycol to a concentration of 1 to 2 mg per ml; and administering the tripeptide compound at concentrations ranging from 0.5 to 50 µg per ml of the tumor cells for 15 minutes to 24 hours at 37° C.

13. The method of claim 11, wherein 10 mg of the tripeptide is first dissolved in a solution of 0.25 ml of N,N-dimethylacetamide, 0.25 ml of pure ethanol, and 0.5 ml of propylene glycol; preparing the solution by further diluting the dissolved drug in an aqueous solution of 50% propylene glycol so that the stock solutions are concentrated in a range of 1 to 2 mg per ml; exposing the tumor cells to 0.5 to 50 µg of the tripeptide compound per ml of solvent for pulse exposure from 0.25 to 4 hr.

14. The method of claim 11, wherein the tumor cells are either MJY-alpha murine mammary cells or B-16 melanoma cells.

15. The method of claim 14, wherein the tumor cells are in a layer density of approximately $2 \times 10^5$ cells per sq. cm. of well.

16. The method of claim 11, wherein the tumor cells are a member selected from a group consisting of rabbit, marmoset, murine L-1210 and primary human leukemias.

17. The method of claim 16, wherein the tumor cells are at cell concentrations of $6–10 \times 10^5$ cells/ml.

* * * * *